(12) United States Patent
Kalchauer et al.

(10) Patent No.: US 6,175,030 B1
(45) Date of Patent: Jan. 16, 2001

(54) PROCESS FOR THE PREPARATION OF ORGANOCHLOROSILANES

(75) Inventors: Wilfried Kalchauer, Burghausen; Herbert Straussberger; Willibald Streckel, both of Mehring/Öd; Ulrich Goetze, Burghausen, all of (DE)

(73) Assignee: Wacker-Chemie GmbH, Munich (DE)

( * ) Notice: Under 35 U.S.C. 154(b), the term of this patent shall be extended for 0 days.

(21) Appl. No.: 09/523,600

(22) Filed: Mar. 13, 2000

(30) Foreign Application Priority Data

Apr. 27, 1999 (DE) .............................................. 199 19 337

(51) Int. Cl.⁷ ....................................................... C07F 7/16
(52) U.S. Cl. ................................................................ 556/472
(58) Field of Search ............................................... 556/472

(56) References Cited

U.S. PATENT DOCUMENTS

| Re. 33,452 | 11/1990 | Ward, III et al. . |
| 4,554,370 | 11/1985 | Ward, III et al. . |
| 5,306,328 | 4/1994 | Streckel et al. . |
| 5,777,146 | * 7/1998 | Straussberger et al. ............. 556/472 |
| 5,981,784 | * 11/1999 | Kalchauer et al. .................. 556/472 |

* cited by examiner

*Primary Examiner*—Paul F. Shaver
(74) *Attorney, Agent, or Firm*—Brooks & Kushman P.C.

(57) ABSTRACT

In a process for the direct synthesis of methylchlorosilanes, chloromethane is reacted with a catalyst composition comprising silicon, copper catalyst, zinc promoter and pyrogenic silicic acid.

20 Claims, No Drawings

PROCESS FOR THE PREPARATION OF ORGANOCHLOROSILANES

TECHNICAL FIELD

The invention relates to a process for the direct synthesis of methylchlorosilanes using a catalyst composition comprising pyrogenic silicic acid.

BACKGROUND ART

Processes for the preparation of methylchlorosilanes by reacting silicon with chloromethane in the direct Muller-Rochow synthesis in the presence of suitable catalysts and catalyst combinations have already been disclosed. For example, U.S. Reissue Pat. No. 33,452 describes a direct synthetic method using a catalyst combination of copper or copper compounds with zinc and tin co-catalysts. The ratio of copper, zinc and tin catalysts to one another has a considerable effect on the process, in particular on productivity and selectivity, while the form in which the catalysts are introduced into the catalyst composition, for example as metal, alloys or compounds, is of secondary importance.

U.S. Pat. No. 4,554,370 describes a process in which silicon is reacted with chloromethane in the presence of copper(I) chloride as catalyst, and in the presence of pyrogenic silicic acid as an anti-agglomerant, to give methylchlorosilanes. The presence of pyrogenic silicic acid is intended to prevent the formation of agglomerates in the "contact mass", composed of silicon and catalysts.

DISCLOSURE OF INVENTION

The principle aim of the direct synthesis is to prepare dimethyldichlorosilane, required for the preparation of linear polysiloxanes, as inexpensively as possible, in the most environmentally friendly manner possible, in high yields, and with a high space/performance ratio. A process which requires lesser amounts of catalysts for comparable selectivity and reactivity is both less expensive and also more environmentally friendly, since the spent catalysts must either be reprocessed or converted into a form suitable for disposal to landfill. The object of the present invention is to provide a process for the direct synthesis of methylchlorosilanes by the Müller-Rochow method in which, while retaining reactivity and selectivity, the concentration of copper catalyst or promoter in the catalyst composition can be reduced. Thus the invention relates to a process for the direct synthesis of methylchlorosilanes wherein chloromethane is reacted with a catalyst composition comprising silicon, copper catalyst, zinc promoter and pyrogenic silicic acid. The addition of pyrogenic silicic acid to the catalyst composition allows the concentration of copper catalyst and/or zinc promoter to be reduced without having an adverse effect on reactivity and/or selectivity. Moreover, the pyrogenic silicic acid used in the process is enviroinentally acceptable without further treatment since it consists exclusively of $SiO_2$.

BEST MODE FOR CARRYING OUT THE INVENTION

The organochlorosilane process of the subject invention can be carried out batchwise or continuously. In industrial production, only the continuous version is used. "Continuous" means that the amounts of silicon reacted and the amount of catalysts and promoters discharged with the reaction dust are continuously replenished, preferably as a pre-mixed catalyst composition. The continuous direct synthesis is preferably carried out in fluidized-bed reactors, in which chloromethane is simultaneously used as both fluidizing medium and reactant.

The silicon required is ground to a powder in advance and mixed with copper catalyst and promoters to give the catalyst composition. Silicon is preferably employed in a maximum particle size of 700 $\mu$m, particularly preferably in a maximum particle size of 500 $\mu$m and a minimum particle size of 20 $\mu$m. The silicon employed usually has a purity of >98%.

A production campaign for the continuous direct synthesis is started with the induction phase. To commence the induction phase, methyl chloride is passed into the heated catalyst composition. The induction phase is followed by the initiation phase, in which the crude silane formation commences. The reaction initially proceeds with low selectivity and reactivity. The stable production phase is subsequently reached. Silicon and, where necessary, catalysts and promoters/co-catalysts are continuously replenished. The production campaign ends when chloromethane is no longer passed into the catalyst composition.

In the case of continuous operation of a reactor, the production rates, based on the target product dimethyldichlorosilane, drop in a production campaign after a substantially stable production phase. For this reason, the production campaign must be terminated after a certain time. A production campaign usually lasts from only a few days to several weeks. After termination of a production campaign, the reactor is emptied, refilled with silicon, copper catalyst and promoters/co-catalysts, and restored to the reaction conditions.

In the direct synthesis, unreacted chloromethane, gaseous methylchlorosilanes and any entrained particles exit the reactor. The entrained particles consist of reacted silicon particles, fine silicon particles, catalysts, and promoters/co-catalysts. If desired, the entrained particles can be separated from the gas stream via one or more cyclones, it being possible for large entrained particles of the catalyst composition to be fed back into the reactor. The silane is subsequently separated from residual dust components and unreacted chloromethane and fed to distillation. Purified, unreacted chloromethane can be recirculated into the reactor.

The process is preferably carried out in a fluidized-bed reactor, preferably at a temperature in the range from 250 to 400° C., in particular at from 250 to 360° C. The process is usually carried out at the pressure of the ambient atmosphere, i.e. at from about 0.1 MPa to 0.5 MPa, since this requires the least complication although higher pressures can also be used.

The process can also be carried out using inert gases, such as, for example, nitrogen or argon. Preferably, no inert gas is used.

In a preferred embodiment, the amount and velocity of the gas stream is selected such that a fluidized bed of catalyst composition and gas is formed in the reactor. The mixture of silicon, catalysts, promoters and pyrogenic silicic acid is referred to as the "catalyst composition". Unreacted chloromethane and inert gas, if used, and gaseous methylchlorosilanes leave the reactor. If desired, the entrained particles can be separated from the gas stream via one or more cyclones, large entrained particles of the catalyst composition being fed back into the reactor. The catalyst composition is prepared by simple mixing of the individual components at room temperature. Treatment of the catalyst composition before introduction into the reactor is possible, but is not carried out in the preferred embodiment.

In a particularly preferred embodiment, the pyrogenic silicic acid is firstly mixed with the copper catalyst and/or the zinc promoter, since this increases the flowability of the catalyst system and, depending on the silicic acid employed, reduces the hygroscopic action of various catalyst components and thus considerably improves the handling properties.

In the process according to the invention, the form of the copper (a) is preferably selected from metallic copper, copper alloys, copper oxide and copper chloride. Copper oxide can be, for example, copper in the form of copper oxide mixtures and in the form of copper(II) oxide. Copper chloride can be in the form of CuCl or in the form of $CuCl_2$, with corresponding mixtures also being possible. In a preferred embodiment, the copper is employed as copper oxide and/or as CuCl. It is preferred to use from 0.3 to 10% by weight, more preferably from 0.5 to 7% by weight, and most preferably from 0.5 to 4.5% by weight of copper catalyst, based on metallic copper and silicon.

In the process according to the invention, zinc (b) is preferably employed in the form of metallic zinc, or alternatively as an alloy with copper and, if desired, further promoters, or in the form of zinc oxide or zinc chloride. The amount of zinc employed is preferably from 0.3 to 60% by weight, more preferably from 0.8 to 40% by weight, and most preferably from 1 to 20% by weight, based on copper and zinc as metal.

In the process according to the invention, further promoters (c) besides zinc can be employed. These are preferably selected from phosphorus, cesium, barium, iron, and in particular tin and antimony. Antimony and/or tin (c) are preferably employed as metals or alloys. The amount of antimony and/or tin employed is preferably in total from 200 to 8000 ppm, more preferably from 300 to 4000 ppm, and most preferably from 500 to 3000 ppm, based on the copper employed, calculated as metal.

In the process according to the invention, pyrogenic silicic acid, (d) preferably pyrogenic silicic acid which has been hydrophobicized by surface treatment, is employed. The surface treatment can be carried out, for example, using organosilanes or organosiloxanes or by etherification of hydroxyl groups to alkoxy groups. The pyrogenic silicic acid preferably has a BET surface area of at least 50 m²/g. Pyrogenic silicic acids with and without surface treatment are commercially available, for example from Wacker-Chemie GmbH under the trade name Wacker® HDK. The amount of pyrogenic silicic acid employed is preferably from 0.3 to 5% by weight, more preferably from 0.5 to 2.5% by weight, based on the total amount of catalysts (a–c) employed. Lower and higher concentrations of pyrogenic silicic acid are possible, but higher concentrations do not give further improvements and at lower concentrations the advantage of the process is reduced.

In a preferred embodiment of the process, at least one of the catalyst components from (a–b) is employed in a non-metallic form; particular preference is given to an embodiment in which both catalyst components (a) and (b) are used in a non-metallic form.

In the examples below, unless stated otherwise in each case, all amounts are by weight, all pressures are 0.10 MPa (abs.), all temperatures are 20° C., and silane M2 is dimethyldichlorosilane.

EXAMPLES

The results achieved by the reaction of silicon with chloromethane in the presence of suitable catalysts depend, in addition to the composition of the catalyst composition, also on the design of the experimental apparatus and on the way in which the experiment is carried out. In order to eliminate the two latter parameters and in order to be able clearly to demonstrate the advantages of the invention, the experiments described in the examples below were carried out by the following standardized procedure.

As silicon powder was used commercially available silicon metal containing the following main contaminants: Al 0.20%, Fe 0.27%, and Ca 0.04%. The silicon was ground and screened to a particle size in the range from 70 to 240 μm. The copper oxide used was prepared as described in U.S. Pat. No. 5,306,328, Example 5. As pyrogenic silicic acid, various grades, commercially available from Wacker-Chemie under the trade name Wacker® HDK, were used. All other chemicals are commercially available on the chemicals market, for example from Fluka Chemie GmbH, Germany.

As the experimental plant was used a laboratory fluidized-bed reactor (vertical glass tube having an internal diameter of 25 mm and a height of 500 mm) with heating coil, gas diffuser frit, distillation bridge with brine cooling, and collecting flask.

The standardized procedure used is as follows: Copper catalyst, zinc co-catalyst, and Wacker-HDK pyrogenic silica are mixed intimately with 8 mg of tin powder, then mixed with 120 g of silicon, introduced into the reactor and heated to 340° C. under a 40 l/h stream of nitrogen. 40 l/h of chloromethane are subsequently passed through the reactor, and the catalyst composition is heated to 395° C. After an induction time, silane formation begins in the region of from 2 to 30 minutes, the reaction temperature is reduced to 360° C., and 50 ml of methylchlorosilanes are collected (initiation phase). Subsequently, a further 30 ml of methylchlorosilanes are collected. The time taken for these 30 ml of silanes to form is known as the production phase. The production rate (PR2) is calculated from the formula:

PR2=(mg of methylchlorosilane in the production phase)/(surface area of the silicon×minutes in the production phase)

The silane composition of the 30 ml of methylchlorosilanes was determined in percent by weight by GC analysis.

Example 1

This example provides evidence that catalyst handling is greatly improved by mixing zinc co-catalyst in the form of $ZnCl_2$ with HDK. $ZnCl_2$ was mixed intimately with 1.0% by weight of Wacker®-HDK-H20 and Wacker®-HDK-H2000 (hydrophobic, pyrogenic silicic acids) and left to stand uncovered at room temperature. In the comparative examples, $ZnCl_2$ was not added to pyrogenic silicic acid. Without addition of HDK, $ZnCl_2$ clumps completely after 3 to 4 hours owing to its hygroscopic properties. With addition of 1% of HDKD® H-20 pyrogenic silicic acid to the $ZnCl_2$, the material is still fully flowable even after storage in air for 4 hours.

With addition of 1% of HDK® H-2000 pyrogenic silicic acid to the $ZnCl_2$, the material is still fully flowable even after storage in air for 30 days.

Examples 2–9

These examples provide evidence that the concentration of the Zn component can be reduced in the $CuCl/ZnCl_2/Sn$ catalyst system by addition of pyrogenic silicic acid without the reactivity simultaneously being reduced. Without addition of pyrogenic silicic acid, this effect is not observed. Examples 2–5 are not examples according to the invention.

| Example | CuCl(g) | $ZnCl_2$(g) | HDK ®-H2000(g) | PR2 | % silane M2 |
|---------|---------|-------------|----------------|-----|-------------|
| 2 | 5 | 1.7 | 0 | 63 | 81.2 |
| 3 | 5 | 1.0 | 0 | 55 | 85.5 |
| 4 | 5 | 0.5 | 0 | 46 | 85.3 |
| 5 | 5 | 0.1 | 0 | PR2 not reached after 5 hours | |
| 6 | 5 | 1.7 | 0.07 | 64 | 81.2 |
| 7 | 5 | 1.0 | 0.06 | 62 | 83.9 |
| 8 | 5 | 0.5 | 0.06 | 65 | 85.1 |
| 9 | 5 | 0.1 | 0.05 | 64 | 84.5 |

Examples 10–14 13

These examples provide evidence that the concentration of the Zn component can be reduced in the CuO/ZnO/Sn catalyst system by addition of pyrogenic silicic acid without the reactivity simultaneously being reduced. Without addition of pyrogenic silicic acid, this effect is not observed. Examples 10–11 are not examples according to the invention.

| Example | CuO(g) | $ZnO_2$(g) | HDK ®-H2000(g) | PR2 | % silane M2 |
|---------|--------|------------|----------------|-----|-------------|
| 10 | 6 | 1 | 0 | 58 | 84.9 |
| 11 | 6 | 0.1 | 0 | PR2 not reached after 5 hours | |
| 12 | 6 | 1 | 0.07 | 61 | 84.5 |
| 13 | 6 | 0.1 | 0.06 | 65 | 84.6 |

Examples 14–19

These examples provide evidence that the concentration of the Cu catalyst can be reduced in the $CuCl/ZnCl_2/Sn$ catalyst system by addition of pyrogenic silicic acid without the reactivity simultaneously being reduced. Without addition of pyrogenic silicic acid, this effect is not observed. The pyrogenic silicic acid concentration was likewise varied in Examples 17–19. Examples 14–16 are not examples according to the invention.

| Example | CuCl(g) | $ZnCl_2$(g) | HDK ®-H2000(g) | PR2 | % silane M2 |
|---------|---------|-------------|----------------|-----|-------------|
| 14 | 7.3 | 1.7 | 0 | 65 | 81.4 |
| 15 | 6.0 | 1.7 | 0 | 64 | 79.5 |
| 16 | 4.0 | 1.7 | 0 | 48 | 72.6 |
| 17 | 7.3 | 1.7 | 0.09 | 68 | 81.5 |
| 18 | 6.0 | 1.7 | 0.16 | 97 | 82.0 |
| 19 | 4.0 | 1.7 | 0.06 | 67 | 75.4 |

Examples 20–24

These examples provide evidence that the HDK grade in the $CuO/ZnCl_2/Sn$ catalyst system has an effect on the maintenance of reactivity with a reduced amount of Zn. Examples 20–21 are not examples according to the invention. H-20 and H2000 are hydrophobic, pyrogenic silicic acids, while N-20 is a hydrophilic, pyrogenic silicic acid.

| Example | CuO(g) | $ZnCl_2$(g) | HDK(g) | PR2 | % silane M2 |
|---------|--------|-------------|--------|-----|-------------|
| 20 | 6 | 1.7 | 0 | 68 | 80.8 |
| 21 | 6 | 0.3 | 0 | 50 | 81.4 |
| 22 | 6 | 0.3 | 0.06 [N-20] | 58 | 80.8 |
| 23 | 6 | 0.3 | 0.06 [H-20] | 62 | 80.8 |
| 24 | 6 | 0.3 | 0.06 [H-2000] | 68 | 82.2 |

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for the direct synthesis of methylchlorosilanes by reacting chloromethane with a catalyst composition comprising silicon, copper catalyst, zinc promoter and, an effective production rate-increasing amount of pyrogenic silicic acid.

2. The process of claim 1, wherein the process is carried out continuously.

3. The process of claim 1, in which the form of copper is one or more metallic copper, copper alloys, copper oxide, or copper chloride.

4. The process of claim 2, in which the form of copper is one or more metallic copper, copper alloys, copper oxide, or copper chloride.

5. The process of claim 1, in which in addition to zinc, tin and/or antimony are employed as further promoters.

6. The process of claim 2, in which in addition to zinc, tin and/or antimony are employed as further promoters.

7. The process of claim 3, in which in addition to zinc, tin and/or antimony are employed as further promoters.

8. The process of claim 4, in which in addition to zinc, tin and/or antimony are employed as further promoters.

9. The process of claim 1, wherein said pyrogenic silicic acid is employed in an amount of 0.3% to 5% based on the amount of said catalyst composition.

10. The process of claim 2, wherein said pyrogenic silicic acid is employed in an amount of 0.3% to 5% based on the amount of said catalyst composition.

11. The process of claim 3, wherein said pyrogenic silicic acid is employed in an amount of 0.3% to 5% based on the amount of said catalyst composition.

12. The process of claim 5, wherein said pyrogenic silicic acid is employed in an amount of 0.3% to 5% based on the amount of said catalyst composition.

13. The process of claim 1, wherein said pyrogenic silicic acid is hydrophobic pyrogenic silicic acid.

14. The process of claim 3, wherein said pyrogenic silicic acid is hydrophobic pyrogenic silicic acid.

15. The process of claim 5, wherein said pyrogenic silicic acid is hydrophobic pyrogenic silicic acid.

16. The process of claim 9, wherein said pyrogenic silicic acid is hydrophobic pyrogenic silicic acid.

17. The process of claim 1 wherein one or more of copper catalyst, zinc co-catalyst, or tin or antimony promoter is decreased in concentration as compared to a similar direct synthesis not employing pyrogenic silicic acid, said decrease in concentration not decreasing the reactivity and/or selectivity to dimethyldichlorosilane of said direct synthesis as compared to said similar direct synthesis not employing pyrogenic silicic acid.

18. The process of claim 1, wherein said pyrogenic silicic acid is first contacted with one or both of copper catalyst and/or zinc co-catalyst prior to contacting with chloromethane.

19. The process of claim 1, wherein a hygroscopic salt of zinc is contacted with said pyrogenic silicic acid to form a free flowing zinc-containing pyrogenic silicic acid composition.

20. The process of claim 19, wherein said pyrogenic silicic is hydrophobic pyrogenic silicic acid.

* * * * *